(12) United States Patent
Weston et al.

(10) Patent No.: US 9,550,684 B2
(45) Date of Patent: Jan. 24, 2017

(54) PROCESS FOR MAKING MOLECULAR SIEVES

(71) Applicant: ExxonMobil Chemical Patents Inc., Baytown, TX (US)

(72) Inventors: Simon C. Weston, Annandale, NJ (US); Hilda B. Vroman, Piscataway, NJ (US); Karl G. Strohmaier, Port Murray, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/891,537

(22) PCT Filed: May 5, 2014

(86) PCT No.: PCT/US2014/036761
§ 371 (c)(1),
(2) Date: Nov. 16, 2015

(87) PCT Pub. No.: WO2014/200633
PCT Pub. Date: Dec. 18, 2014

(65) Prior Publication Data
US 2016/0090308 A1 Mar. 31, 2016

Related U.S. Application Data

(60) Provisional application No. 61/833,349, filed on Jun. 10, 2013.

(30) Foreign Application Priority Data

Aug. 9, 2013 (EP) .................................... 13179951

(51) Int. Cl.
C07C 2/02 (2006.01)
C01B 33/36 (2006.01)
(Continued)

(52) U.S. Cl.
CPC ............ *C01B 39/04* (2013.01); *B01J 29/7026* (2013.01); *B01J 35/002* (2013.01); *C01B 39/48* (2013.01);
(Continued)

(58) Field of Classification Search
CPC ......... C10G 50/00; C01B 39/04; C01B 39/48; B01J 35/002; B01J 29/7026; C07C 2/02; C07C 2529/70
(Continued)

(56) References Cited

U.S. PATENT DOCUMENTS 4,391,785 A 7/1983 Rosinski et al.
4,873,067 A 10/1989 Valyocsik et al.

FOREIGN PATENT DOCUMENTS

WO 2013/055871 4/2013
WO WO2013/055871 A1 * 4/2013

OTHER PUBLICATIONS

Han et al., "Diquatemary (CH3)(C2H5)N+(CH2)nN+(C2H5)(CH3)2 and (C2H5)2—(CH3)N+(CH2)nN+(CH3)(C2H5)2 ions with n = 4-6 as structure-directing agents in zeolite synthesis", Elsevier, 2005, pp. 183-189.*

(Continued)

*Primary Examiner* — William Cheung

(57) ABSTRACT

The invention relates to a process for preparing molecular sieves, such as ZSM-57, using one or more structure directing agents selected from the group consisting of $N^1,N^1,N^5,N^5$-tetraethyl-$N^1,N^5$-dimethylpentane-1,5-diaminium, 1-ethyl-1-(5-(1-methylpiperidin-1-ium-1-yl)pentyl)piperidin-1-ium, 1,1'-(hexane-1,6-diyl)bis(1-ethylpiperidin-1-ium), and 1,1-diethylpyrrolidin-1-ium.

25 Claims, 3 Drawing Sheets

(51) Int. Cl.
  *C01B 39/00* (2006.01)
  *C08F 210/00* (2006.01)
  *C01B 39/04* (2006.01)
  *C01B 39/48* (2006.01)
  *C10G 50/00* (2006.01)
  *B01J 29/70* (2006.01)
  *B01J 35/00* (2006.01)

(52) U.S. Cl.
  CPC ............... *C07C 2/02* (2013.01); *C10G 50/00* (2013.01); *C07C 2529/70* (2013.01)

(58) Field of Classification Search
  USPC .................. 585/533; 423/700, 704; 526/348
  See application file for complete search history.

(56) References Cited

OTHER PUBLICATIONS

Baerlocher et al., "Atlas of Zeolite Framework Types", Elsevier, Sixth Revised Edition, 2007.

Han et al., "Diquaternary $(CH_3)(C_2H_5)N^+(CH_2)_nN^+(C_2H_5)(CH_3)_2$ and $(C_2H_5)_2(CH_3)N^+(CH_2)_nN^+(CH_3)(C_2H_5)_2$ ions with n = 4-6 as structure-directing agents in zeolite synthesis", Elsevier, 2005, pp. 183-189.

Han et al., "Zeolite Synthesis Using Flexible Diquaternary Alkylammonium Ions $(C_nH_{2n+1})_2HN^+H(C_nH_{2n+1})_2$ with n = 1-5 as Structure-Directing Agents", Chem. Mater. 2005, vol. 17, pp. 477-486.

Lee et al., "Synthesis and Characterization of ERI-Type UZM-12 Zeolites and Their Methanol-to-Olefin Performance", J. Am. Chem. Soc. 2010, vol. 132, pp. 12971-12982.

Lee et al., "Zeolite synthesis in the presence of flexible diquaternary alkylammonium ions $(C_2H_5)_3N^+(CH_2)_nN^+(C_2H_5)_3$ with n = 3-10 as structure-directing agents", Microporous and Mesoporous Materials 60, (2003), pp. 237-249.

Lee et al., "Reinvestigation into the synthesis of zeolites using diquaternary alkylammonium ions $(CH_3)_3N^+(CH_2)_nN^+(CH_3)_3$ with n = 3-10 as structure-directing agents", Microporous and Mesoporous Materials 68 (2004), pp. 97-104.

Mertens et al., "Tailored Alkene Oligomerization with H-ZSM-57 Zeolite", Angew. Chem. Int. Ed. 2000, vol. 39, pp. 4376-4379.

\* cited by examiner

PROCESS FOR MAKING MOLECULAR SIEVES

I. CROSS REFERENCE TO RELATED APPLICATIONS

This application is a National Stage Application of International Application No. PCT/US2014/036761 filed May 5, 2014, which claims priority to and the benefit of U.S. Provisional Application No. 61/833,349, filed Jun. 10, 2013, and European Application No. 13179951.2, filed Aug. 9, 2013, all of which are incorporated herein by reference in their entireties.

FIELD

The present invention relates to a process for making a molecular sieve, a molecular sieve as made by the process and to processes for converting a feedstock using the molecular sieve.

BACKGROUND

Molecular sieve materials, both natural and synthetic, have been demonstrated in the past to be useful as adsorbents and to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Within the crystalline molecular sieve material there are a large number of cavities which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as rigid three-dimensional framework of $SiO_4$ and Periodic Table Group 13 element oxide (e.g., $AlO_4$). The tetrahedra are cross-linked by the sharing of oxygen atoms with the electrovalence of the tetrahedra containing the Group 13 element (e.g., aluminum or boron) being balanced by the inclusion in the crystal of a cation, for example, a proton, an alkali metal or an alkaline earth metal cation. This can be expressed wherein the ratio of the Group 13 element (e.g., aluminum or boron) to the number of various cations, such as $H^+$, $Ca^{2+}/2$, $Sr^{2+}/2$, $Na^+$, $K^+$, or $Li^+$, is equal to unity.

Molecular sieves that find application in catalysis include any of the naturally occurring or synthetic crystalline molecular sieves. Examples of these molecular sieves include large pore zeolites, intermediate pore size zeolites, and small pore zeolites. These zeolites and their isotypes are described in "Atlas of Zeolite Framework Types", eds. Ch. Baerlocher, L. B. McCusker, D. H. Olson, Elsevier, Sixth Revised Edition, 2007, which is hereby incorporated by reference. A large pore zeolite generally has a pore size of at least about 6.5 Å to 7 Å and includes LTL, MAZ, FAU, OFF, *BEA, and MOR framework type zeolites (IUPAC Commission of Zeolite Nomenclature). Examples of large pore zeolites include mazzite, offretite, zeolite L, zeolite Y, zeolite X, omega, and beta. An intermediate pore size zeolite generally has a pore size from about 4.5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, MCM-22, silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, SAPO-34, SAPO-35, ZK-14, SAPO-42, ZK-21, ZK-22, ZK-5, ZK-20, zeolite A, chabazite, zeolite T, and ALPO-17.

One known synthetic zeolite is ZSM-57. The preparation of ZSM-57 and its characterization using X-ray diffraction is described in U.S. Pat. No. 4,873,067 and since its discovery ZSM-57 has been made and used commercially as a catalyst for olefin oligomerization. Known methods of preparing ZSM-57 all use the same structure directing agent as disclosed in U.S. Pat. No. 4,873,067 namely $N^1,N^1,N^1,N^5,N^5,N^5$-hexaethylpentane-1,5-diaminium cation (structure I).

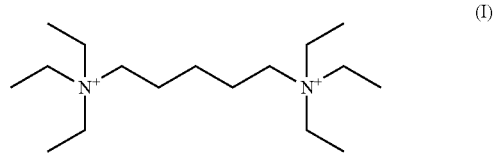 [SMILES: CC[N+](CC)(CC)CCCCC[N+](CC)(CC)CC]

(I)

$N^1,N^1,N^1,N^5,N^5,N^5$-hexaethylpentane-1,5-diaminium

A wide range of structure directing agents have been used to make other molecular sieves. For example, Joo Hyuck Lee et al, JACS, 2010, 132, 12971-12982, discloses a synthesis of UZM-12 (framework type ERI) using a number of cationic structure directing agents including $N^1,N^1,N^5$, $N^5$-tetraethyl-$N^1,N^5$-dimethylpentane-1,5-diaminium cation. However, it is desirable to identify new structure directing agents for the preparation of molecular sieves, and in particular for the preparation of ZSM-57.

According to the present invention, new structure directing agents are provided for the synthesis of a variety of molecular sieves, including ZSM-57.

SUMMARY

In one respect the invention provides a process of making a molecular sieve comprising the steps of:
a. preparing a synthesis mixture comprising a source of tetravalent tetrahedral atoms Y, a source of water and at least one structure directing agent (SDA) selected from the group consisting of the following cations:

(II) $N^1,N^1,N^5,N^5$-tetraethyl-$N^1,N^5$-dimethylpentane-1,5-diaminium

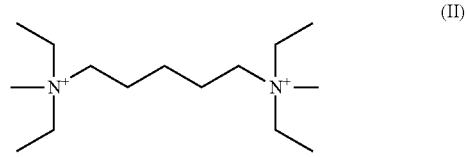

(II)

(III) 1-ethyl-1-(5-(1-methylpiperidin-1-ium-1-yl)pentyl)piperidin-1-ium

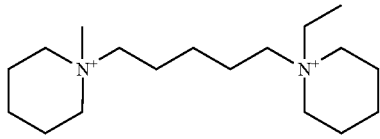

(IV) 1,1'-(hexane-1,6-diyl)bis(1-ethylpiperidin-1-ium)

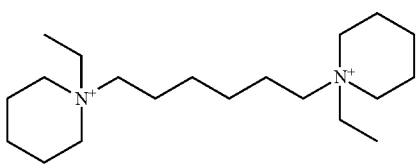

(V) 1,1-diethylpyrrolidin-1-ium

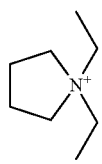

Optionally, a source of alkali metal ions Z and optionally, a source of trivalent tetrahedral atoms X;
b. maintaining said synthesis mixture under crystallization conditions until the molecular sieve has formed, and
c. separating the molecular sieve from the synthesis mixture,
provided, that when the synthesis mixture comprises cation (II), the molecular sieve product is not UZM-12.

Optionally, the molecular sieve prepared by the process is ZSM-57. Optionally, the process of the invention also further comprises the step of calcining the as-synthesized molecular sieve.

The invention also provides in a further aspect, a molecular sieve in its as-synthesized form made according to the process of the invention.

In a further aspect, the invention provides a process for converting a feedstock comprising an organic compound which comprises the step of contacting said feedstock at organic compound conversion conditions with a catalyst comprising an active form of the molecular sieve prepared by the process of the invention.

DETAILED DESCRIPTION OF EMBODIMENTS

Figure 1:
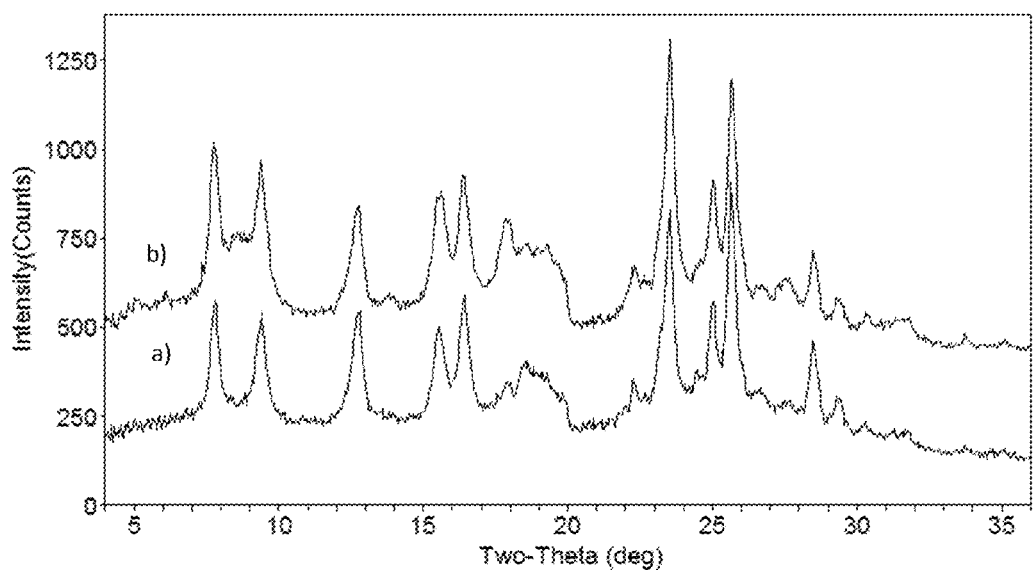
FIG. 1 shows the X-ray diffraction pattern of the synthesized zeolites of Example 1 (lower line a) and Example 2 (upper line b).

Described herein is a process for making a molecular sieve involving at least one structure directing agent selected from a specified group of cations shown above of structural formula II, III, IV and V. Those structure directing agents may be used to prepare a wide variety of molecular sieves. Of particular interest are molecular sieves of the MFS framework type, for example, ZSM-57. Many of the aspects of the invention will be illustrated by reference to the preparation of ZSM-57 below, but it should be noted that the invention is not in any way limited to the preparation of ZSM-57.

Prior to the date of the present invention, it has generally previously understood that there was only one structure directing agent, which was known to promote the formation of ZSM-57. That known structure directing agent is $N^1,N^1,N^1,N^5,N^5,N^5$-hexaethylpentane-1,5-diaminium (structure I).

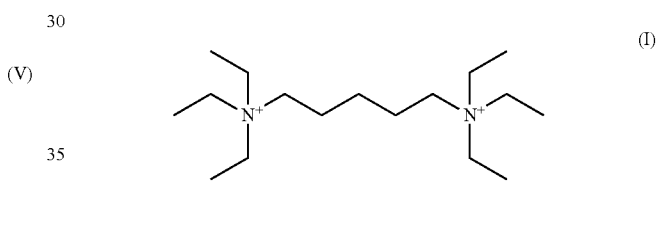

$N^1,N^1,N^1,N^5,N^5,N^5$-hexaethylpentane-1,5-diaminium

One aspect of the present invention is the discovery that ZSM-57 can be prepared using other structure directing agents, in particular, cations of structures of II, III, IV and V. The use of alternative structure directing agents for the preparation of ZSM-57 may make available ZSM-57 having compositions outside the range of known ZSM-57 compositions and may also allow greater control over crystal morphology and size. Furthermore, the use of structure directing agent V is likely to reduce cost as compared to the process involving the currently known structure directing agent.

When the synthesis mixture comprises a cation of structure II, the molecular sieve produced is one other than UZM-12. Optionally, in the process of the invention the molecular sieve produced is not UZM-12, even in the case where the synthesis mixture does not comprise a cation of structure II. Preferably, the molecular sieve produced in the process of the invention is of the MFS framework type, for example, ZSM-57. The MFS framework consists of unidimensional, ten-ring pores with lobes at the intersection of eight-ring channels along the second direction. ZSM-57 has been found to give very high selectivity to $C_8$ products for the acid catalyzed reaction of butene molecules compared to other 10-ring zeolites (J. A. Martens et al., *Angew. Chem. Int. Ed.* 2000, 39, 4376). ZSM-57 is currently used commercially to catalyze the oligomerization of olefins.

The structure directing agents II, III, IV and V, will typically be added to the synthesis mixture in the form of a salt, or a solution thereof, including a suitable anion, for example, hydroxide anion. The term "structure directing agent" as used herein should be taken to include salts comprising the cations II, III, IV and V, where such meaning is consistent with the context.

Optionally, the synthesis mixture comprises at least one structure directing agent selected from the group consisting of cations III, IV and V. Optionally, the synthesis mixture comprises cation V as the structure directing agent.

Optionally, the synthesis mixture has a composition falling within the following molar ratios:

| | |
|---|---|
| $YO_2/X_2O_3 =$ | 4-200 |
| $H_2O/YO_2 =$ | 10-200 |
| $OH^-/YO_2 =$ | 0-3 |
| $Z/YO_2 =$ | 0-3 |
| $SDA/YO_2 =$ | 0.01-2 | in which Z is an alkali metal ion and SDA is the structure directing agent. Optionally, Y=Si.

Optionally, the synthesis mixture comprises a source of trivalent tetrahedral atom X. Optionally, X=Al. In a preferred embodiment, Y=Si and X=Al and the molecular sieve is an aluminosilicate.

In one embodiment, the synthesis mixture does not comprise a source of the trivalent tetrahedral atom X. In an alternative embodiment, the synthesis mixture does comprise a source of trivalent tetrahedral atom X and the ratio of $YO_2/X_2O_3$ is in the range from 4 to 200, and may be in the range of from 15 to 100, such as from 20 to 50.

Optionally, the ratio $H_2O/YO_2$ is in the range of 10 to 200, for example, from 20 to 50.

Preferably, the synthesis mixture is alkaline, that is it comprises hydroxide ion. However, in some embodiments, for example, where fluoride ion is present in the synthesis mixture, the synthesis mixture may be acidic. Optionally, the ratio $OH^-/YO_2$ is in the range of from 0 to 3, preferably 0.1 to 1.0, for example 0.2 to 0.5.

Optionally, the synthesis mixture does not comprise a source of an alkali metal ion Z. However, in a preferred embodiment, the synthesis mixture does comprise an alkali metal ion Z. Optionally, the alkali metal ion Z is $Na^+$ or $K^+$ or a mixture thereof. Preferably, Z is $K^+$. Optionally, the ratio $Z/YO_2$ is in the range of from 0 to 3, preferably, 0 to 2, for example 0.1 to 1.0.

The structure directing agent may be present in any suitable amount, for example, the ratio $SDA/YO_2$ may be in the range of from 0.01 to 2, and is preferably in the range of from 0.01 to 1, for example, in the range of from 0.1 to 0.4.

Optionally, the synthesis mixture has a composition falling within the following molar ratios:

| | |
|---|---|
| $YO_2/X_2O_3 =$ | 15-100 |
| $H_2O/YO_2 =$ | 20-50 |
| $H_2O/YO_2 =$ | 0.1-1.0 |
| $Z/YO_2 =$ | 0-2 |
| $SDA/YO_2 =$ | 0.1-1 |

The crystallization of the molecular sieve from the synthesis mixture can be carried out at either static or stirred conditions in a suitable reactor vessel, such as polypropylene jars or Teflon lined, or stainless steel autoclaves. The temperature may be, for example, in the range of from 80° C. to 250° C., such as from about 100° C. to about 200° C., for example, from about 150° C. to about 170° C. for a time sufficient for crystallization to occur at the temperature used. That time may, for example, be from about 12 hours to about 100 days, optionally, from 12 hours to 60 days, optionally, from about 1 day to 50 days, for example, from 1 day to 30 days. Thereafter, as-synthesized crystals are separated from the synthesis mixture and recovered.

The synthesis may be aided by seeds from a previous synthesis of a molecular sieve, for example, ZSM-57 seeds. The seeds may suitably be present in an amount of from about 0.01 ppm by weight to about 10,000 ppm by weight such as from about 100 ppm by weight to about 5,000 ppm by weight of the synthesis mixture.

To the extent desired and depending on the $YO_2/X_2O_3$ molar ratio of the material, any cations in the as synthesized molecular sieve can be replaced in accordance with techniques well known in the art by ion exchange with other cations. Preferred replacing cations include metal ions, hydrogen ions, hydrogen precursor, e.g., ammonium ions and mixtures thereof. Particularly preferred cations are those which tailor the catalytic activity for certain reactions, for example, hydrocarbon conversion reactions or olefin oligomerization reactions. These include hydrogen, rare earth metals and metals of groups 2 to 15 of the periodic table of elements. As used herein, the numbering scheme for the periodic table groups is as disclosed in Chemical & Engineering News, 63(5), 27(1985).

The invention also provides a molecular sieve in its as-synthesized form made by the process of the invention. The as-synthesized molecular sieve will include in its pores at least some of the structure directing agent which was present in the synthesis mixture.

The process of the invention may further comprise the step of calcining the as-synthesized molecular sieve. That treatment will remove a portion of, or the entire amount of organic SDA used in its synthesis. This is conveniently done by thermal treatment (calcination) in which the as-synthesized molecular sieve is heated at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

The molecular sieve produced by the process of the invention may be intimately combined with a hydrogenating component, such as molybdenum, rhenium, nickel, cobalt, chromium, manganese, or a noble metal such as platinum or palladium where a hydrogenation-dehydrogenation function is to be performed. Such component can be in the composition by way of co-crystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include, chloroplatinic acid, platinous chloride and various compounds containing the platinum amine complex.

The molecular sieve produced by the process of the invention, when employed either as an adsorbent or as a catalyst should be dehydrated, at least partially. This can be done by heating to a temperature in the range of about 100° C. to about 500° C., such as about 200° C. to about 370° C.

in an atmosphere such as air, nitrogen, etc., and at atmospheric, subatmospheric or superatmospheric pressures for between 30 minutes and 48 hours. Dehydration can also be performed at room temperature merely by placing the molecular sieve in a vacuum, but a longer time is required to obtain a sufficient amount of dehydration.

The molecular sieve may be used as an adsorbent or as a catalyst to catalyze a wide variety of organic compound conversion processes including many of present commercial/industrial importance. Examples of chemical conversion processes which are effectively catalyzed by the molecular sieve, by itself or in combination with one or more other catalytically active substances including other crystalline catalysts, include those requiring a catalyst with acid activity. Examples of organic conversion processes which may be catalyzed by molecular sieves include cracking, hydrocracking, disproportionation, alkylation, and isomerization.

The invention provides a process for converting a feedstock comprising an organic compound which comprises the step of contacting said feedstock at organic compound conversion conditions with a catalyst comprising an active form of the molecular sieve prepared by the process of the invention. That process for converting a feedstock may be, for example, an olefin oligomerization process, especially when the molecular sieve is ZSM-57.

As in the case of many catalysts, it may be desirable to incorporate the molecular sieve, with another material resistant to the temperatures, and other conditions employed in organic conversion processes. Such materials include active and inactive materials and synthetic or naturally occurring zeolites, as well as, inorganic materials such as clays, silica and/or metal oxides such as alumina. The latter may be either naturally occurring or in the form of gelatinous precipitates or gels including mixtures of silica and metal oxides. Use of a material in conjunction with the molecular sieve, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained in an economic and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the molecular sieve include, the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the molecular sieve also include, inorganic oxides, such as silica, zirconia, titania, magnesia, beryllia, alumina, and mixtures thereof.

In addition to the foregoing materials, the molecular sieve can be composited with a porous matrix material such as silica-alumina, silica-magnesia, silica-zirconia, silica-thoria, silica-beryllia, silica-titania, as well as, ternary compositions such as silica-alumina-thoria, silica-alumina-zirconia, silica-alumina-magnesia and silica-magnesia-zirconia.

The relative proportions of the molecular sieve and inorganic oxide matrix may vary widely, with the molecular sieve content ranging from about 1 to about 90 percent by weight and more usually, particularly when the composite is prepared in the form of beads, in the range of about 2 wt. % to about 80 wt. % of the composite.

The invention will now be more particularly described with reference to the following non-limiting Examples and the accompanying drawings.

The Structure Directing Agents (SDAs)

Structure Directing Agent (II) is commercially available from SACHEM.

Preparation of SDA III

1-Ethylpiperidine and 1-methylpiperidine with 1,5-dibromopentane

Step 1: Mono addition of 1-methylpiperidine to 1,5-dibromopentane

To a stirring solution of 1,5-dibromopropane (81.7 mL, 600 mmol) in DMF (40 mL) was added 1-methylpiperidine (29.1 mL, 240 mmol) in DMF (120 mL) by liquid addition funnel over the course of a day. After the addition, the reaction mixture was allowed to stir at room temperature for an additional 3 days. A solid had precipitated, which was removed by vacuum filtration; this is the undesired double addition product. The clear orange filtrate was slowly poured into ether (1.5 L) to precipitate the desired mono addition product overnight. The next day additional ether (750 mL) was added to the precipitating mono addition product. The precipitated mono addition product was collected by vacuum filtration and washed with fresh ether (500 mL) before drying in the vacuum oven at 80° C. $^1$H NMR confirmed that the off white solid that had precipitated from ether was the desired mono addition product in good purity, the compound was saved as for reaction in the next step (39.25 g, 50%).

Step 2: Reaction of the mono addition product with 1-ethylpiperidine

To a 1 L round bottom flask was added the mono addition product (39.25 g, 119 mmol), DMF (100 mL), and 1-ethylpiperidine (18.86 g, 166.6 mmol) before allowing the reaction mixture to stir at room temperature for 6 days. After 5 days additional DMF (100 mL) was added to the mixture. During the reaction period a white precipitate formed, which was then collected by vacuum filtration, washed with ether (2×~100 mL), and dried in the vacuum oven at 80° C. $^1$H NMR confirmed the structure of the desired product in good purity (33.64 g, 64%).

Conversion to Hydroxide

The bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt. %. The concentration was confirmed by acid-base titration and by $^1$H NMR. The concentration in this case was 19.8 wt. %.

Preparation of SDA IV 1-ethylpiperidine and 1,6-dibromohexane

To a 1 L round bottom flask was added 1-ethylpiperidine (87.0 mL, 625 mmol), DMF (250 mL) and 1,6-dibromohexane (39.0 mL, 250 mmol). The reaction was allowed to stir for three days while the product precipitated out of solution in a mildly exothermic reaction. Next, the precipitate was vacuum filtered, washed with ether (3×~100 mL) and dried in the vacuum oven at 70° C. A $^1$H NMR of the dried solid revealed incomplete reaction, as well as, several impurities, so it was placed back into a 1 L round bottom flask and dissolved in DMF (320 mL) before adding additional 1-ethylpiperidine (38.0 mL) and allowing reaction to occur at room temperature for 27 days. The precipitate was vacuum filtered, washed with ether (3×~100 mL) and dried in the vacuum oven at 70° C. $^1$H NMR confirmed the structure of the desired product in good purity (94.70 g, 81%).

Conversion to Hydroxide

The bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt. %. The concentration was confirmed by acid-base titration and by $^1$H NMR. The concentration in this case was 17.08 wt. %.

Preparation of SDA V

Synthesis of 1,1-diethylpyrrolidin-1-ium iodide

To a $N_2$ purged flask ethanol (500 mL), pyrrolidine (35.56 g) and potassium carbonate (69.1 g) were added. To this stirred mixture iodoethane (233.95 g) was added slowly. The mixture was then refluxed for 4 days under $N_2$ in darkness. After cooling to ~10° C. the solids were vacuum filtered and washed with cold ethanol (500 mL). The mother liquor and ethanol wash were then combined and evaporated under vacuum to give an orange solid (112.15 g, 88% yield). This orange solid was then extracted with chloroform (500 mL) twice, the chloroform extracts gravity filtered and evaporated under vacuum to give a sticky orange solid (105.98 g, 83% yield) which was then dried in a vacuum desiccator for 11 days to give a tan solid (91.94 g, 72% yield). This tan solid was then crystallized from hot acetone, cooled to room temperature, the solids vacuum filtered and washed with cold ether (100 mL). This solid was then dried in a vacuum desiccator overnight and then further dried at 80° C. under vacuum (1 mbar) for 2 hours to give a light tan solid (84.69 g, 66% yield). $^1$H and $^{13}$C NMR confirmed the structure of the desired product in good purity.

Conversion to Hydroxide

The bromide was subsequently converted to a hydroxide solution by column ion-exchange using an excess of MTO-DOWEX SBR LCNG(OH) resin. Distilled water was eluted through the column until the pH was less than 11 and the resulting solution concentrated to the desired concentration, typically ~20 wt. %. The concentration was confirmed by acid-base titration and by $^1$H NMR. The concentration in this case was 23.28 wt. %.

EXAMPLE 1

A zeolite reaction slurry was prepared by adding, with stirring, 104.9 mg of distilled water, 134.1 mg of 23.2 wt. % $N^1,N^1,N^5,N^5$-tetraethyl-$N^1,N^5$-dimethylpentane-1,5-diaminium hydroxide (SDA II), 146.9 mg of Ludox LS-30 colloidal silica (30.4 wt. % $SiO_2$ in water), 56.6 mg of 17.5 wt. % KOH, 16.9 mg of potassium aluminate solution (11.2 wt. % $Al_2O_3$, 15.3 wt. % KOH), and 40.7 mg of 20 wt. % HCl to a 1.5 mL stainless steel reactor. The mixture had the following mole ratios:

| | |
|---|---|
| SDA/Si = | 0.15 |
| OH$^-$/Si = | 0.6 |
| K$^+$/Si = | 0.3 |
| $SiO_2/Al_2O_3$ = | 40 |
| $H_2O$/Si = | 30.3 |

The reactor was sealed and then placed in a 160° C. tumbling oven (40 rpm) for 7 days. The product was recovered by centrifugation, washed with distilled water and then dried in air. Phase analysis by powder X-ray diffraction showed the crystalline material to be ZSM-57 as indicated in FIG. 1, line (a).

EXAMPLE 2

A zeolite reaction slurry was prepared by adding, with stirring, 71.3 mg of distilled water, 134.3 mg of 23.2 wt. % $N^1,N^1,N^5,N^5$ tetraethyl-$N^1,N^5$-dimethylpentane-1,5-diaminium hydroxide (SDA II), 147.2 mg of Ludox LS-30 colloidal silica (30.4 wt. % $SiO_2$ in water), 64.1 mg of 17.5 wt. % KOH, 42.4 mg of potassium aluminate solution (2.24 wt. % $Al_2O_3$, 3.06 wt. % KOH), and 40.7 mg of 20 wt. % HCl to a 1.5 mL stainless steel reactor. The mixture had the following mole ratios:

| | |
|---|---|
| SDA/Si = | 0.15 |
| OH$^-$/Si = | 0.6 |
| K$^+$/Si = | 0.3 |
| $SiO_2/Al_2O_3$ = | 80 |
| $H_2O$/Si = | 30.3 |

Figure 2:
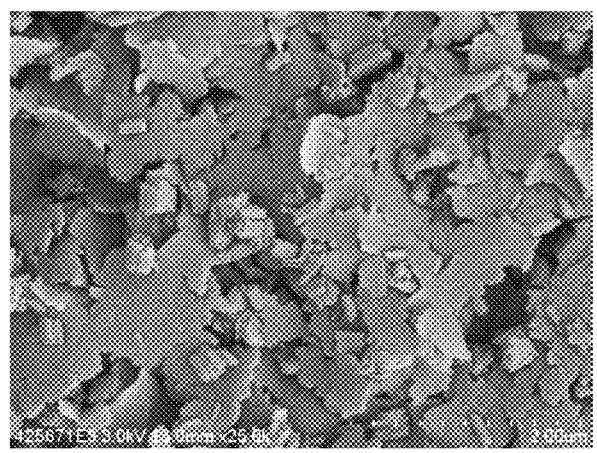
FIG. 2 shows a scanning electron micrograph of the synthesized zeolite of Example 2.

The reactor was sealed and then placed in a 160° C. tumbling oven (40 rpm) for 7 days. The product was recovered by centrifugation, washed with distilled water and then dried in air. Phase analysis by powder X-ray diffraction showed the crystalline material to be ZSM-57 as indicated in FIG. 1, line (b). A scanning electron micrograph SEM of the product is shown in FIG. 2.

EXAMPLE 3

A zeolite reaction slurry was prepared by adding, with stirring, 20.2 mg of distilled water, 145.7 mg of Ludox LS-30 colloidal silica (30.1 wt. % $SiO_2$ in water), 176.7 mg of 19.8 wt. % 1-ethyl-1-(5-(1-methylpiperidin-1-ium-1-yl)pentyl)piperidin-1-ium hydroxide (SDA III), 70.7 mg of 17.5 wt. % KOH, 26.2 mg of 15 wt. % aluminum nitrate, and 60.5 mg of 10 wt. % HCl to a 1.5 mL stainless steel reactor. The mixture had the following mole ratios:

| | |
|---|---|
| SDA/Si = | 0.15 |
| OH$^-$/Si = | 0.6 |
| K$^+$/Si = | 0.3 |
| $SiO_2/Al_2O_3$ = | 80 |
| $H_2O$/Si = | 30.3 |

Figure 3:
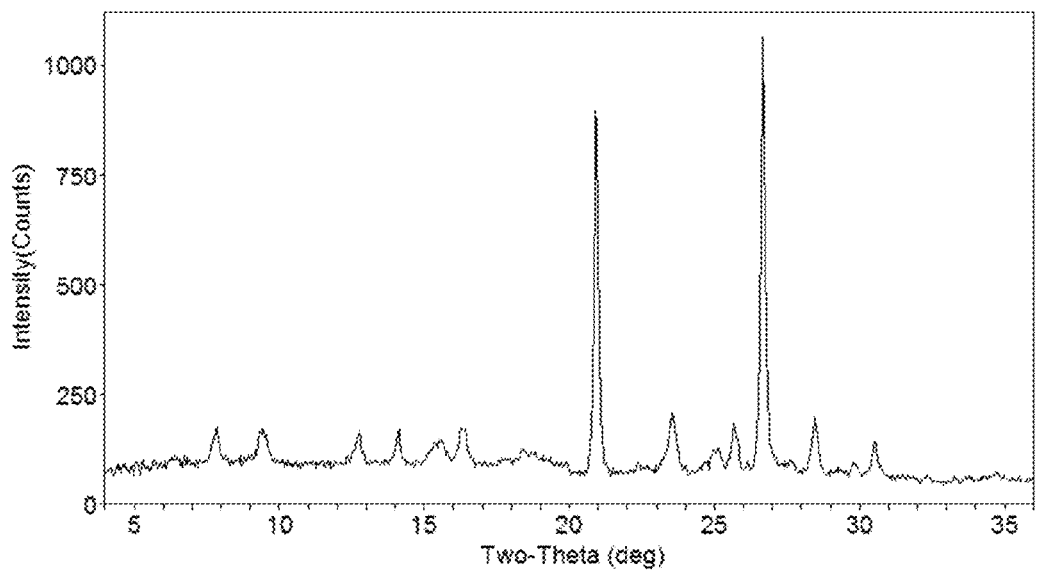
FIG. 3 shows the X-ray diffraction pattern of the synthesized zeolite of Example 3.

The reactor was sealed and then placed in a 160° C. tumbling oven (60 rpm) for 28 days. The product was recovered by centrifugation, washed with distilled water and then dried in air. Phase analysis by powder X-ray diffraction showed the crystalline material to be ZSM-57 contaminated with quartz as indicated in FIG. 3.

EXAMPLE 4

A zeolite reaction slurry was prepared by adding, with stirring, 0.9 mg of distilled water, 110.3 mg of Ludox LS-30 colloidal silica (30.1 wt. % SiO₂ in water), 250.9 mg of 17.1 wt. % 1,1'-(hexane-1,6-diyl)bis(1-ethylpiperidin-1-ium) hydroxide (SDA IV), 98.7 mg of 20 wt. % KBr, and 39.2 mg of 15 wt. % aluminum nitrate to a 1.5 mL stainless steel reactor. The mixture had the following mole ratios:

| | |
|---|---|
| SDA/Si = | 0.225 |
| OH⁻/Si = | 0.45 |
| K⁺/Si = | 0.3 |
| SiO₂/Al₂O₃ = | 40 |
| H₂O/Si = | 40.225 |

Figure 4:
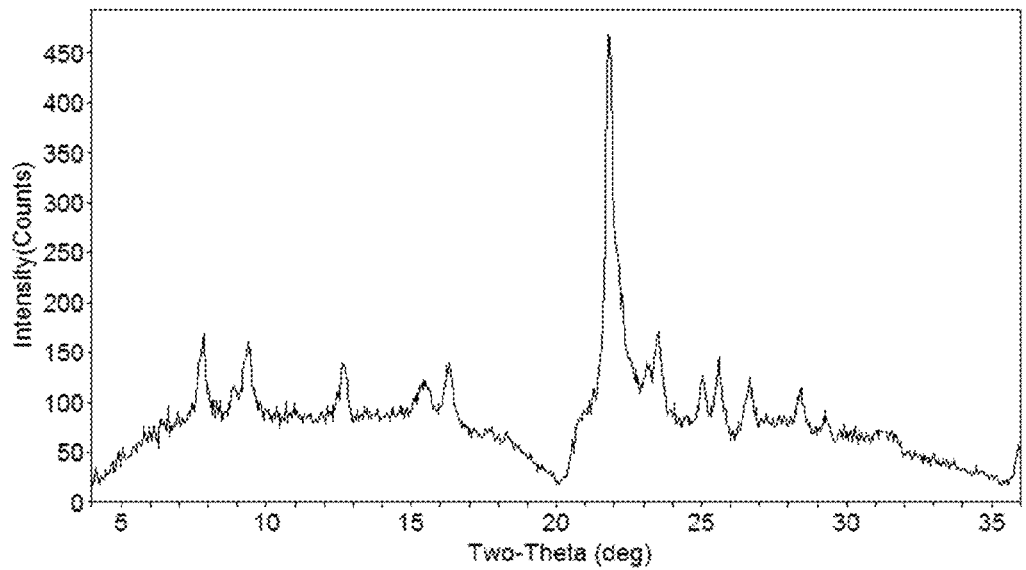
FIG. 4 shows the X-ray diffraction pattern of the zeolite of Example 4.

The reactor was sealed and then placed in a 160° C. tumbling oven (30 rpm) for 28 days. The product was recovered by centrifugation, washed with distilled water and then dried in air. Phase analysis by powder X-ray diffraction showed the crystalline material to be ZSM-57 contaminated with cristobalite and quartz as indicated in FIG. 4.

EXAMPLE 5

A zeolite reaction slurry was prepared by adding, with stirring, 63.6 mg of distilled water, 146.1 mg of Ludox LS-30 colloidal silica (30.2 wt. % SiO₂ in water), 137.4 mg of 23.3 wt. % 1,1-diethylpyrrolidin-1-ium hydroxide (SDA V), 35.2 mg of 17.5 wt. % KOH, 65.5 mg of 20 wt. % KBr, and 52.1 mg of 15 wt. % aluminum nitrate to a 1.5 mL stainless steel reactor. The mixture had the following mole ratios:

| | |
|---|---|
| SDA/Si = | 0.30 |
| OH⁻/Si = | 0.45 |
| K⁺/Si = | 0.3 |
| SiO₂/Al₂O₃ = | 40 |
| H₂O/Si = | 30.225 |

Figure 5:
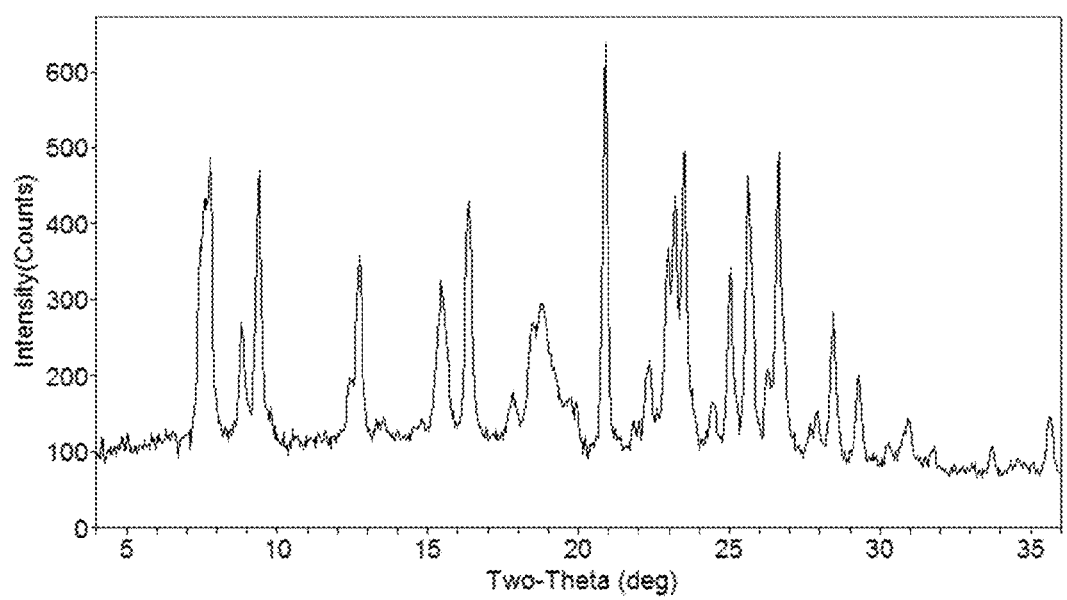
FIG. 5 shows the X-ray diffraction pattern of the zeolite of Example 5.

The reactor was sealed and then placed in a 160° C. tumbling oven (30 rpm) for 28 days. The product was recovered by centrifugation, washed with distilled water and then dried in air. Phase analysis by powder X-ray diffraction showed the crystalline material to be ZSM-57 contaminated with ZSM-12 and quartz as indicated in FIG. 5.

The present invention has been described and illustrated by reference to particular embodiments, those of ordinary skill in the art will appreciate that the invention lends itself to variations not necessary illustrated herein. For this reason, then, reference should be made solely to the appended claims for purposes of determining the true scope of the present invention.

The invention claimed is:

1. A process for making a molecular sieve comprising the steps of:
   (a) preparing a synthesis mixture comprising a source of tetravalent tetrahedral atoms Y, optionally a source of alkali metal ions Z, optionally a source of trivalent tetrahedral atoms X, a source of water and at least one structure directing agent (SDA) selected from the group consisting of the following cations:

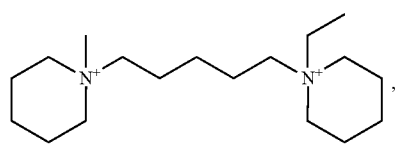
(III)

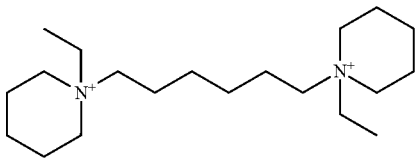
(IV) and

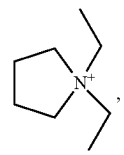
(V) , (b) maintaining the synthesis mixture under crystallization conditions until the molecular sieve has formed, and
   (c) separating the molecular sieve from the synthesis mixture.

2. The process of claim 1, wherein the synthesis mixture comprises at least one SDA selected from the group consisting of cation (III), cation (IV) and cation (V), and the molecular sieve is of the MFS framework type.

3. The process of claim 1, wherein the molecular sieve is ZSM-57.

4. The process of claim 1, wherein the synthesis mixture has a composition falling within the following molar ratios:

| | |
|---|---|
| YO₂/X₂O₃ = | 4-200 |
| H₂O/YO₂ = | 10-200 |
| OH⁻/YO₂ = | 0-3 |
| Z/YO₂ = | 0-3 |
| SDA/YO₂ = | 0.01-2 | wherein X is a trivalent tetrahedral atom, Y is a tetravalent tetrahedral atom, Z is an alkali metal ion and SDA is the structure directing agent.

5. The process of claim 4, wherein the synthesis mixture has a composition within the following molar ratios:

| | |
|---|---|
| YO₂/X₂O₃ = | 15-100 |
| H₂O/YO₂ = | 20-50 |
| H₂O/YO₂ = | 0.1-1.0 |
| Z/YO₂ = | 0-2 |
| SDA/YO₂ = | 0.1-1. |

6. The process of claim 1, wherein the synthesis mixture comprises a cation of structure (V):

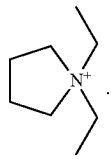
(V) .

7. The process of claim 1, wherein the synthesis mixture comprises a cation of structure (IV):

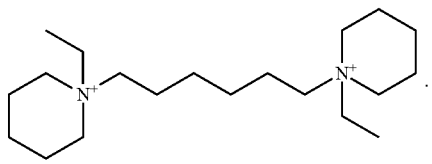

(IV)

8. The process of claim 1, wherein the synthesis mixture is maintained under crystallization conditions including a temperature in the range of from 80° C. to 250° C. for a duration in the range of from 12 hours to 60 days.

9. The process of claim 1, wherein the synthesis mixture comprises potassium ions.

10. The process of claim 1, wherein X is aluminum and Y is silicon.

11. The process of claim 1, further comprising a step of calcining the molecular sieve.

12. A process for converting a feedstock comprising an organic compound which comprises the step of contacting said feedstock at organic compound conversion conditions with a catalyst comprising an active form of the molecular sieve prepared by the process of claim 1.

13. The process of claim 12, wherein the process for converting a feedstock is an olefin oligomerization process.

14. A molecular sieve in its as-synthesised form made by the process of claim 2 which comprises the at least one SDA selected from the group consisting of cation (III), cation (IV) and cation (V).

15. A process for making a molecular sieve of MFS framework type, the process comprising the steps of:

(a) preparing a synthesis mixture comprising a source of tetravalent tetrahedral atoms Y, optionally a source of alkali metal ions Z, optionally a source of trivalent tetrahedral atoms X, a source of water and at least one structure directing agent (SDA) which comprises a cation of structure (II):

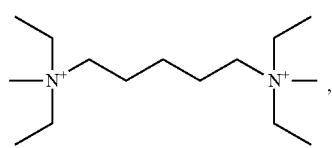

(II)

(b) maintaining the synthesis mixture under crystallization conditions until the molecular sieve of a MFS framework type has formed, and (c) separating the molecular sieve of a MFS framework type from the synthesis mixture.

16. The process of claim 15, wherein the molecular sieve is ZSM-57.

17. The process of claim 15, wherein the synthesis mixture has a composition falling within the following molar ratios:

| |
|---|
| $YO_2/X_2O_3$ = 4-200 |
| $H_2O/YO_2$ = 10-200 |
| $OH^-/YO_2$ = 0-3 |
| $Z/YO_2$ = 0-3 |
| $SDA/YO_2$ = 0.01-2 | wherein X is a trivalent tetrahedral atom, Y is a tetravalent tetrahedral atom, Z is an alkali metal ion and SDA is the structure directing agent.

18. The process of claim 17, wherein the synthesis mixture has a composition within the following molar ratios:

| |
|---|
| $YO_2/X_2O_3$ = 15-100 |
| $H_2O/YO_2$ = 20-50 |
| $H_2O/YO_2$ = 0.1-1.0 |
| $Z/YO_2$ = 0-2 |
| $SDA/YO_2$ = 0.1-1. |

19. The process of claim 15, wherein the synthesis mixture is maintained under crystallization conditions including a temperature in the range of from 80° C. to 250° C. for a duration in the range of from 12 hours to 60 days.

20. The process of claim 15, wherein the synthesis mixture comprises potassium ions.

21. The process of claim 15, wherein X is aluminum and Y is silicon.

22. The process of claim 15, further comprising a step of calcining the molecular sieve of a MFS framework type.

23. A process for converting a feedstock comprising an organic compound which comprises the step of contacting said feedstock at organic compound conversion conditions with a catalyst comprising an active form of the molecular sieve of a MFS framework type prepared by the process of claim 15.

24. The process of claim 23, wherein the process for converting a feedstock is an olefin oligomerization process.

25. A molecular sieve in its as-synthesised form of the MFS framework type made by the process of claim 15 which comprises the SDA of cation (II).

* * * * *